(12) United States Patent
Yanagisawa et al.

(10) Patent No.: US 8,900,524 B2
(45) Date of Patent: Dec. 2, 2014

(54) OPTICAL SENSOR

(75) Inventors: Masahiro Yanagisawa, Tokyo (JP);
Takuya Nakanishi, Tokyo (JP);
Naonobu Shimamoto, Tokyo (JP);
Mikiko Saito, Tokyo (JP); Tetsuya Osaka, Tokyo (JP)

(73) Assignee: Waseda University, Tokyo (JP)

( * ) Notice: Subject to any disclaimer, the term of this patent is extended or adjusted under 35 U.S.C. 154(b) by 675 days.

(21) Appl. No.: 12/934,237

(22) PCT Filed: Mar. 17, 2009

(86) PCT No.: PCT/JP2009/055200
§ 371 (c)(1),
(2), (4) Date: Oct. 22, 2010

(87) PCT Pub. No.: WO2009/119391
PCT Pub. Date: Oct. 1, 2009

(65) Prior Publication Data
US 2011/0051142 A1    Mar. 3, 2011

(30) Foreign Application Priority Data

Mar. 25, 2008    (JP) ................ 2008-079049

(51) Int. Cl.
*G01N 33/543* (2006.01)
*G01N 21/55* (2014.01)
*G01N 21/65* (2006.01)

(52) U.S. Cl.
CPC ............ *G01N 21/554* (2013.01); *G01N 21/658* (2013.01)
USPC ......................................... 422/402; 250/225

(58) Field of Classification Search
USPC ........ 436/518; 250/226, 225, 491.1; 356/445; 422/402
See application file for complete search history.

(56) References Cited

U.S. PATENT DOCUMENTS

| | | | |
|---|---|---|---|
| 5,994,150 A | 11/1999 | Challener et al. | |
| 6,277,653 B1 * | 8/2001 | Challener et al. | ............. 436/518 |
| 7,456,383 B2 | 11/2008 | Kim et al. | |
| 7,927,822 B2 * | 4/2011 | Genick et al. | .................. 435/7.2 |
| 2006/0273245 A1 | 12/2006 | Kim et al. | |

(Continued)

FOREIGN PATENT DOCUMENTS

| | | |
|---|---|---|
| JP | 2005016963 | 1/2005 |
| JP | 2007078621 | 3/2007 |
| JP | 2008014969 | 1/2008 |
| WO | WO2007/094817 | 8/2007 |

OTHER PUBLICATIONS

Sigal et al. (Anal of Chem 1996, 68, 490-497).*

*Primary Examiner* — Sally Merkling
(74) *Attorney, Agent, or Firm* — Duane Morris LLP; J. Rodman Steele, Jr.; Gregory M. Lefkowitz

(57) ABSTRACT

There is provided a novel optical sensor utilizing a surface plasmon resonance technique which is capable of detecting a substance to be detected with high sensitivity independently of a wavelength of irradiated light and is capable of obtaining information, other than a refraction index, on the substance to be detected. At the center of a surface of a metallic film 2 which is formed on a substrate and has no aperture, a circular depression 4 with a diameter of 0.1 to 250 nm is formed and with the depression 4 defined as a center, a plurality of depressions 3 are concentrically formed at intervals of 450 to 530 nm.

15 Claims, 11 Drawing Sheets

(56) References Cited

U.S. PATENT DOCUMENTS

| | | |
|---|---|---|
| 2008/0038841 A1 | 2/2008 | Ezoe et al. |
| 2008/0135739 A1 | 6/2008 | Kim et al. |
| 2009/0073434 A1 | 3/2009 | Kim et al. |
| 2011/0001975 A1* | 1/2011 | Razansky et al. ............. 356/445 |

* cited by examiner

SEM image

Nanoimprint Process

US 8,900,524 B2

OPTICAL SENSOR

CROSS-REFERENCE TO RELATED APPLICATIONS

This application is a §371 national stage entry of International Application No. PCT/JP2009/055200, filed Mar. 17, 2009, and Japanese Patent Application No. 2008-079049, filed Mar. 25, 2008, the entireties of which are hereby incorporated by reference.

TECHNICAL FIELD

The present invention relates to an optical sensor using the surface plasmon resonance method.

BACKGROUND ART

As conventional optical biosensors using the surface plasmon resonance method, there is disclosed, for example, the one having two or more minute openings provided in a metallic film at predetermined intervals (see patent document 1). According to this optical biosensor, surface plasmon waves propagated on an upper side of the metallic film are resonantly phase-aligned, increasing amplitude, and then concentrated on the minute openings. For this reason, a major part of the transmitted light occurring at the lower side of the minute openings comes from components originated from the surface plasmon waves propagated through the upper side of the metallic film, rather than the components of light irradiated directly to the minute openings and transmitted therethrough. Accordingly, detecting the transmitted light occurring at the lower side of the minute openings makes it possible to detect the components of the surface plasmon waves transmitted at the upper side of the metallic film. As the components of the surface plasmon waves contain information about a substance to be detected present at the upper side of the metallic film, the substance can be detected by detecting the transmitted light occurring at the lower side of the minute openings.

Patent document 1 Japanese Un-examined application publication No. 2005-16963

DISCLOSURE OF THE INVENTION

Problems to be solved by the invention

According to this optical biosensor, however, the light transmitted through the minute openings formed through the metallic film is to be observed, and thus, there have been problems that it is impossible to obtain a sufficient intensity of transmitted light in the case that the size of the minute openings is less than wavelength of the irradiated light, and that refractive index is the only information about a substance to be detected that can be obtained from the transmitted light interacting with the surface plasmon waves.

It is, therefore, an object of the present invention to provide a novel optical sensor using the surface plasmon resonance method, said sensor being capable of detecting a substance to be detected, with high sensitivity and without dependency on the wavelength of the irradiation light; and obtaining information other than refractive index about a substance to be detected.

Means for Solving the Problems

An energy conversion device according to the present invention features that a plurality of depressions are formed concentrically at intervals on a surface of a metallic film having no apertures. When light is irradiated to the metallic film, surface plasmon generated on the surface of the metallic film due to surface plasmon resonance is allowed to concentrate on a single point on the metallic film.

An optical sensor according to the present invention includes a substrate and a metallic film which is formed on the substrate and has no apertures. A plurality of depressions are concentrically formed at intervals on the surface of the metallic film.

Further, the optical sensor according to the present invention includes a substrate and a metallic film which is formed on the substrate and has no apertures, in which, at the center of the surface of the metallic film, a circular depression with a diameter of 0.1 to 250 nm is formed and then with this depression defined as a center, a plurality of depressions are concentrically formed at intervals of 450 to 530 nm.

Furthermore, the optical sensor according to the present invention includes a plurality of fan-shaped regions where the intervals of the depressions vary from one region to another.

Moreover, the optical sensor according to the present invention includes a substrate and a metallic film which is formed on the substrate and has no apertures, in which on the surface of the metallic film, two helical protrusions are formed and are joined to each other at each of helical centers thereof, and then, a substantially circular depression with a smaller diameter than a width of the protrusion is formed at the helical center.

Further, the optical sensor according to the present invention includes a substrate and a metallic film which is formed on the substrate and has no apertures, in which on the surface of the metallic film, one helical protrusion is formed, and then, a substantially circular depression with a smaller diameter than a width of the protrusion is formed at the helical center of the helical protrusion.

Furthermore, the optical sensor according to the present invention is formed with a self assembled monolayer on the surface of the metallic film.

Also, the metallic film is made of silver or gold.

Still also, the metallic film is made of silver to which bismuth is added.

Effects of the Invention

According to the energy conversion device of the present invention, a plurality of the depressions are concentrically formed at intervals on the metallic film having no apertures, and thus when light is irradiated onto the metallic film, the surface plasmon generated on the metallic surface by the surface plasmon resonance concentrates on a single point on the metallic film. Hence, the surface plasmon concentrated on the single point is converted into reflected light, permitting the reflected light to radiate Further, according to the optical sensor of the present invention, the optical sensor includes the substrate and the metallic film which is formed on the substrate and has no apertures, and a plurality of the depressions are concentrically formed at intervals on the surface of the metallic film. Accordingly, when light is irradiated, the surface plasmon generated by the surface plasmon resonance concentrates on the center of the concentric depressions. As a result, high-intensity reflected light is generated from the center and then by observing such reflected light, a substance to be detected can be detected with high sensitivity.

Furthermore, the optical sensor includes the substrate and the metallic film which is formed on the substrate and has no apertures, in which at the center of the surface of the metallic film, the circular depression with a diameter of 0.1 to 250 nm is formed, and with the depression defined as a center, a plurality of the depressions are concentrically formed at intervals of 450 to 530 nm, and thus, when light is irradiated, the surface plasmon generated by the surface plasmon resonance concentrates on the depression at the center. As a result, the high-intensity reflected light is generated from the depression at the center and by observing the reflected light, a substance to be detected is detected with high sensitivity.

Moreover, according to the optical sensor of the present invention, the optical sensor includes a plurality of the fan-shaped regions where the intervals of the depressions vary from one region to another. Hence, a plasmon wave can be efficiently converged by selecting a direction according to a specific wavelength of exciting light and then allowing the excited light to polarize in the direction to generate the plasmon resonance.

Still moreover, the optical sensor includes the substrate and the metallic film which is formed on the substrate and has no apertures, in which on the surface of the metallic film, the two helical protrusions are formed and are joined to each other at each of the helical centers of the helical protrusions and then the substantially circular depression with a smaller diameter than the width of the protrusion is formed at the helical center. Hence, in a cross section of the same central angle, the interval between the depressions is bilaterally symmetric and is constant in relation to the center. As the central angle changes, however, the interval between the depressions continuously changes and therefore a plasmon resonance can be generated by excitation lights with continuous wavelengths.

Further, the optical sensor includes the substrate and the metallic film which is formed on the substrate and has no apertures, in which one helical protrusion is formed on the surface of the metallic film, and besides the substantially circular depression with a diameter less than the width of the helical protrusion is formed at the helical center of the helical protrusion. As a result, the interval between the depressions becomes bilaterally asymmetric with respect to the helical center in the cross section at the same angle, and thus a plasmon resonance corresponding to a specific wavelength takes place on one side. There occurs, however, no problem with the convergence to the center, permitting the resolution of a resonant wavelength to increase.

Furthermore, the self-assembled monolayer is formed on the surface of the metallic film, and hence, a biomolecule, as the substance to be detected, is allowed to be adsorbed thereon, permitting the same to be detected with high sensitivity.

Moreover, the metallic film is made of silver or gold, and hence, the efficiency of generating the surface plasmon can be enhanced.

Besides, since the metallic film is made of silver with bismuth added thereto, it is improved in corrosion resistance and heat resistance, while the surface of the metallic film is smoothed, thereby enabling the surface plasmon scattering attributable to the roughness of the surface of the metallic film to be prevented.

BEST MODE FOR CARRYING OUT THE INVENTION

According to an energy conversion device of the present invention, a plurality of depressions are concentrically formed at intervals on a surface of a metallic film having no apertures, so that when light is irradiated onto the metallic film, surface plasmon generated on the metallic film by a surface plasmon resonance is allowed to concentrate on a single point on the metallic film.

Next, a detailed description of preferred examples of an optical sensor, utilizing a principle of this energy conversion device according to the present invention, will be given with reference to the accompanied drawings.

Example 1

Figure 1:
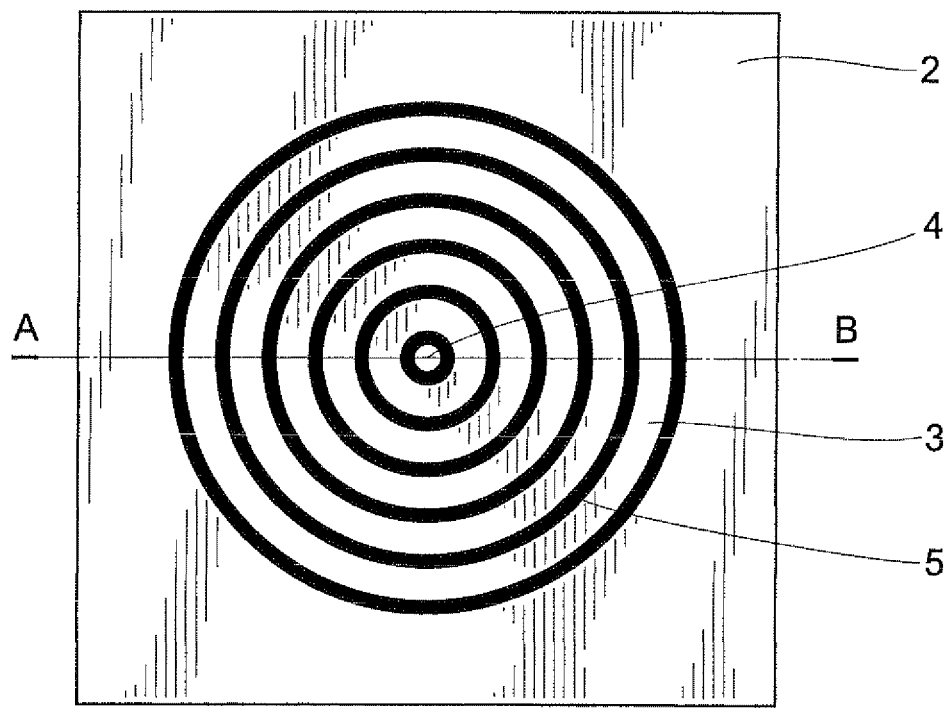
FIG. 1 is a top plan view illustrating an optical sensor according to a first example.
Figure 2:
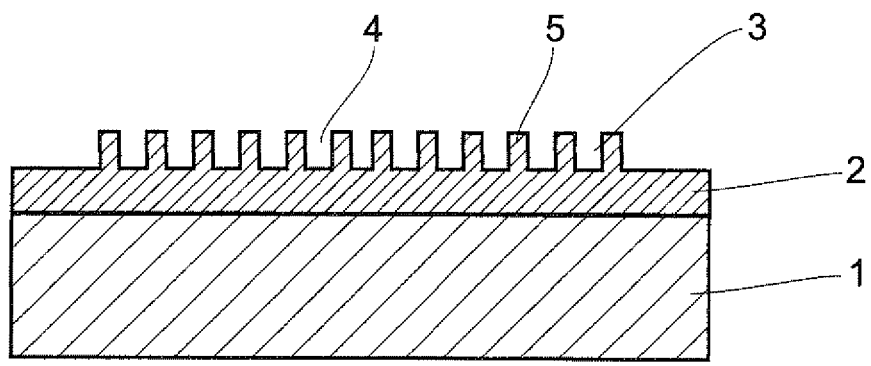
FIG. 2 is a cross-sectional view taken on a line A-B in FIG. 1, illustrating the optical sensor according to the first example.

In FIGS. 1, 2 showing a first example of the optical sensor according to the present invention, numeral 1 denotes a flat and plate-shaped substrate, on which a metallic film 2 is formed. As a material of the substrate 1, any material may be used and it is not limited to any specific one as long as the metallic film 2 can be formed thereon, and thus, quartz, silicon, plastic or the like, for example, may be employed therefor. The metallic film 2 has no apertures and is so thick as to allow no light to be transmitted therethrough. Therefore, the metallic film 2 is desirably 100 nm or more thick even in its thinnest portion.

As a material of the metallic film 2, any material may be used and it is not to be limited to any specific one as long as it allows surface plasmon to be generated, and hence, silver, gold, copper, aluminum or the like may be used therefor. From the viewpoint of the efficiency of generating surface plasmon, silver is most desirable. From the standpoint of corrosion resistance, gold is preferably employed. Further, by adding bismuth to silver, the surface of the metallic film 2 is smoothed, allowing the surface plasmon propagating on the metallic film 2 to be prevented from scattering. Furthermore, by adding bismuth to silver, the metallic film 2 is improved in corrosion resistance and heat resistance. The additive amount of bismuth is desirably 0.05 to 0.2% of the total number of atoms making up the metallic film 2. Adding neodymium instead of bismuth still exerts the same effect.

Alternatively, for the purpose of improving adhesion between the substrate 1 and the metallic film 2, a layer made of chromium or tantalum may be provided between the substrate 1 and the metallic film 2.

On the surface of the metallic film 2, a plurality of depressions 3 are concentrically formed at certain intervals. Preferably, a circular depression 4 with a diameter of 0.1 to 250 nm is formed at the center of the metallic film 2 and then, with this depression 4 defined as a center, a plurality of depressions 3 are concentrically formed in a cyclic fashion at regular intervals. It is desirable that the interval between the depressions 3 be approximately equal to a wavelength of surface plasmon and specifically the interval may be set at 450 to 530 nm.

In addition, it is desirable that the diameter of the depression 4 at the center be smaller than a wavelength of surface plasmon since reflected light described later increases its intensity in that case. Further, size of the depression 4 determines resolution in sensing, and if the size of the depression 4 is 0.1 nm, atomic resolution can be obtained.

Further, each of the depressions 3, 4 has a constant depth and the depth of each of the depressions 3, 4 may desirably be 50 to 200 nm. Furthermore, protrusions 5 with a constant width are formed between the depressions 3. As a result of setting the size of each of the depressions 3, 4 as above, surface plasmon generated by irradiating light onto the entire surface of the metallic film 2 is allowed to efficiently concentrate on the central depression 4.

Figure 3:
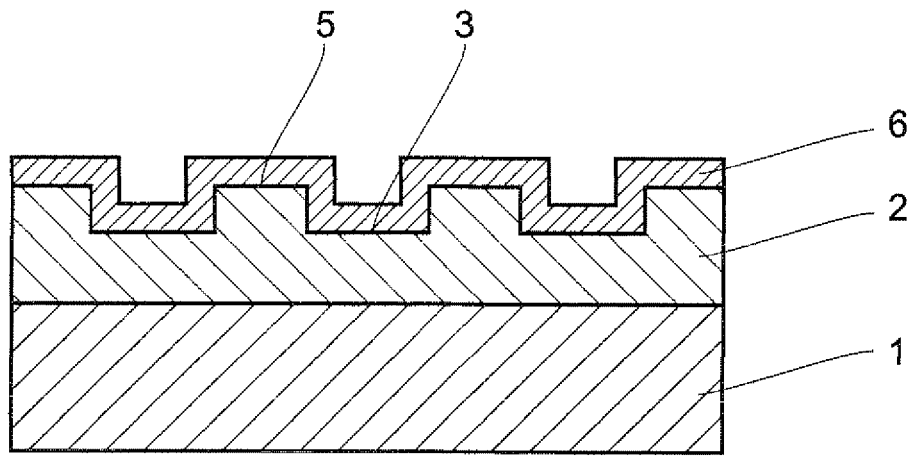
FIG. 3 is an enlarged cross-sectional view illustrating the optical sensor according to the first example.
Figure 4:
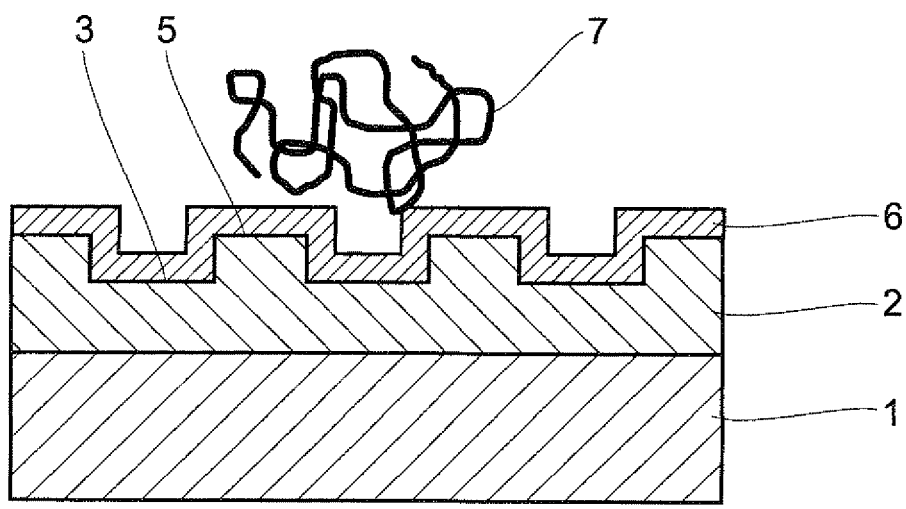
FIG. 4 is an enlarged cross-sectional view illustrating a biological molecule being adsorbed onto the optical sensor according to the first example.

Alternatively, as shown in FIGS. 3, 4, a self-assembled monolayer (an SAM film) 6 may be formed on the surface of the metallic film 2. When the self-assembled monolayer 6 is formed, a biological molecule 7, as a substance to be detected, can be efficiently adsorbed. In the meantime, the self-assembled monolayer 6 is so thin as to be light transmissive, thus exerting no influence on the efficiency of generating surface plasmon on the metallic film 2.

The optical sensor according to the present invention can be fabricated by a process utilizing a known lift-off process, a process utilizing etching or the like. Alternatively, the depressions may be formed on the substrate 1 in advance and then the metallic film 2 may be formed on the depressions, thereby enabling the optical sensor to be fabricated as well.

In the case of forming the self-assembled monolayer 6 on the surface of the metallic film 2, the metallic film 2 including the depressions 3, 4 is formed on the substrate 1, and then, the substrate 1 is immersed in an organic aqueous solution for forming the self-assembled monolayer. Then, by rinsing and drying the substrate 1, the self-assembled monolayer 6 is formed. As for an organic substance for forming the self-assembled monolayer, it is not to be limited to any specific material, but cystamine or the like may preferably be employed.

Next is a description of the behavior of the optical sensor of the present example.

When light is irradiated from a side of the metallic film 2 onto the entire surface of the optical sensor according to the present example, surface plasmon is allowed to occur on the surface of the metallic film 2 due to surface plasmon resonance. This surface plasmon is guided, through a plurality of the depressions 3 concentrically formed at intervals, toward the depression 4 at the center. During this transition, the surface plasmon is allowed to concentrate on the central depression 4 while interacting with a substance to be detected, attached to the surface of the metallic film 2 or a surface of the self-assembled monolayer 6. As a result, high-intensity reflected light is generated which contains information on the substance to be detected and has been intensified by several thousand times. By observing this reflected light, the substance to be detected can be detected and analyzed with high sensitivity.

As for an analysis method, various optical analysis methods such as a Raman analysis method, a fluorescent analysis method and the like can be employed. Consequently, the optical sensor according to the present example can be utilized for an extensive use, such as an ultrasensitive biosensor for detecting an antigen-antibody reaction, DNA and protein; various molecular sensors for detecting sources of aroma and gustatory sensation, and a thin-film structure sensor for a silicon thin film of a solar battery, a protective film comprising a diamond-like carbon used for a magnetic disc, a lubricating film or the like. The optical sensor according to the present invention can be employed as an optical environmental sensor for detecting a volatile organic compound (VOC). VOCs to be detected include gases toxic to human bodies, such as formaldehyde, acetaldehyde, toluene, xylene, paradichlorobenzene, ethyl benzene, styrene, chlorpyrifos, di-n-butyl phthalate, tetradecane, di-n-ethylhexyl phthalate, diazinon and fenobucarb, etc, which are released from electronic devices such a personal computer, building materials or the like.

As described above, the optical sensor according to the present example includes the substrate 1, the metallic film 2 which is formed on the substrate 1 and has no apertures, and a plurality of the depressions 3 concentrically formed at intervals on the surface of the metallic film 2. Accordingly, when light is irradiated, surface plasmon generated by a surface plasmon resonance is allowed to concentrate on the center of the optical sensor. As a result, high-intensity reflected light is generated from the center, thus enabling the detection of a substance to be detected with high sensitivity by observing this reflected light.

Further, the optical sensor according to the present invention includes the substrate 1 and the metallic film 2 formed on the substrate 1, without forming any apertures, in which the circular depression 4 having a diameter of 0.1 to 250 nm is formed on the surface of the metallic film 2 in the center thereof, and a plurality of the depressions 3 are concentrically formed in a cyclic fashion at intervals of 450 to 530 nm with the depression 4 defined as a center. Hence, when light is irradiated, a surface plasmon generated by a surface plasmon resonance concentrates on the depression 4 at the center. As a result, the high-intensity reflected light is generated from the depression 4 at the center and then by observing the reflected light, a substance to be detected can be detected with high sensitivity.

Furthermore, by forming the self-assembled monolayer 6 on the surface of the metallic film 2, biological molecules, being substances to be detected, are adsorbed to the monolayer, thus allowing the biological molecules to be detected with high sensitivity.

Moreover, by making up the metallic film 2 of silver or gold, the efficiency of generating a surface plasmon can be enhanced.

Besides, by making up the metallic film 2 of silver to which bismuth is added, the corrosion resistance and heating resistance of the metallic film 2 can be improved and besides the surface of the metallic film 2 is smoothed, thereby permitting the surface plasmon to be prevented from scattering due to the roughness of the surface of the metallic film 2.

The present invention is not limited to the above example and various modifications are possible. When irradiated light contains two wavelengths, e.g., the depression may be formed not in a concentric fashion but in an elliptical fashion. Further, between the substrate and the metallic film, a film of the other metal may be formed.

The present invention is described in more detail below by specific examples.

A 5 nm-thick chromium film was formed on a substrate made up of quartz by a sputtering process. Then, a 1.00 nm-thick metallic film made up of silver was further formed on the chromium film by a sputtering process. Afterward, a resist was applied on the metallic film to form a concentric resist pattern by applying exposure and development and a metallic film was again formed on the resist pattern to a 100 nm thickness. Next, by removing the resist using a lift-off process, a plurality of concentric protrusions made up of the same metal was formed on the surface of the metallic film, thereby concentrically forming a plurality of depressions in a cyclic fashion at the intervals of 490 nm between a plurality of the concentric protrusions. The thickness of the protrusion at this time, i.e., the depth of the depression was 100 nm. In addition, a circular depression was formed at the center of the concentric circle.

Thereafter, the substrate was immersed in a cystamine aqueous solution and by rising and drying the substrate; the self-assembled monolayer was formed on the metallic film.

Figure 5:
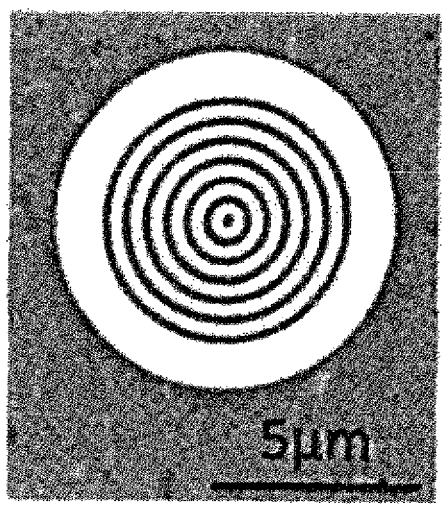
FIG. 5 is an SEM image of the optical sensor according to the first example.

An SEM image of the optical sensor thus produced is shown in FIG. 5.

Figure 6:
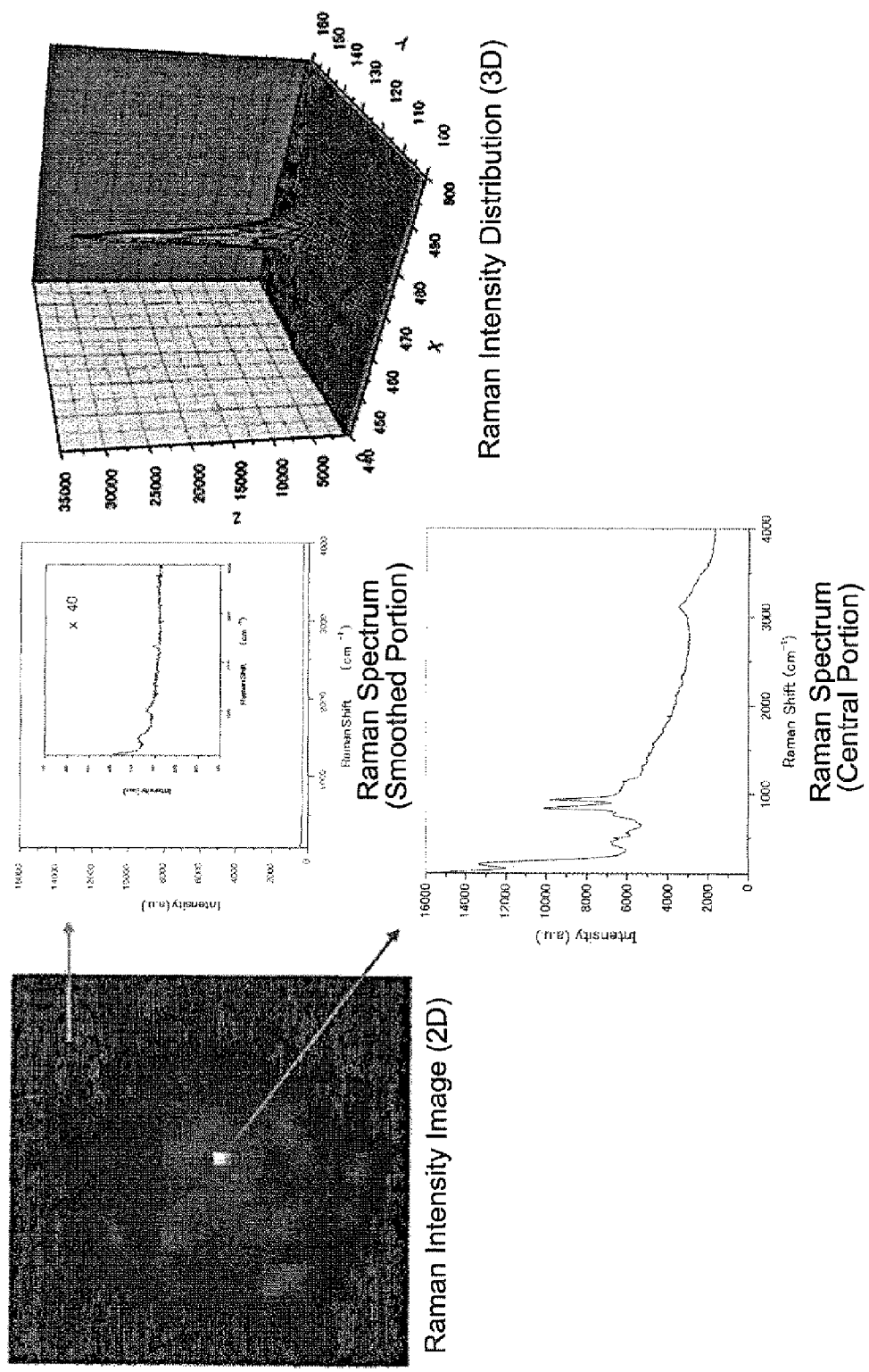
FIG. 6 is a Raman intensity image, Raman spectra and a Raman intensity distribution chart, illustrating results of Raman spectroscopy.

Next, light with a wavelength of 532 nm was irradiated to the optical sensor thus produced to perform a Raman analysis. As a result, as shown in FIG. 6, the high-intensity Raman light intensified by about 2,000 times was observed from the center of the optical sensor as a reflected light. Then, from the reflected light coming from the center of the optical sensor, a Raman spectrum of the self-assembled monolayer formed from cystamine could be obtained with high sensitivity.

Hereunder, other examples of the optical sensor according to the present invention are described. In addition, the same symbols are attached to parts the same as in the example 1 with the detailed description thereof omitted.

Example 2

In the present example, an optical sensor used for multi-wavelength excitation light is exemplified.

An intensity of Raman scattering light differs depending on an excitation wavelength. Molecules are known in which a Raman intensity is increased by a resonant Raman effect in applying wavelengths in the region of short wavelengths or ultraviolet wavelengths.

For example, ultraviolet lights with wavelengths of 200 nm and 488 nm cause the resonant Raman effect in hemoglobin, a short wavelength of 465.8 nm causes the same in β-carotin and an excitation light with a wavelength of 257 nm causes the same in perfluoropolyether used for a lubricant agent of a magnetic disc.

Thus, since the resonant Raman effect is caused by various wavelengths, it is difficult to cover all the wavelengths by a laser optical source with a single wavelength. On the other hand, when utilizing a wide-wavelength optical source and an ultrawideband high-intensity coherent optical source by applying a Xe lump and an Hg lump as an excitation optical source, a wide-wavelength region ranging from that of the infrared to that of the ultraviolet is applicable. If a sensor for a single pitch is employed, however, the wide-wavelength region is hard to cover.

(1) Pattern A

Figure 7:
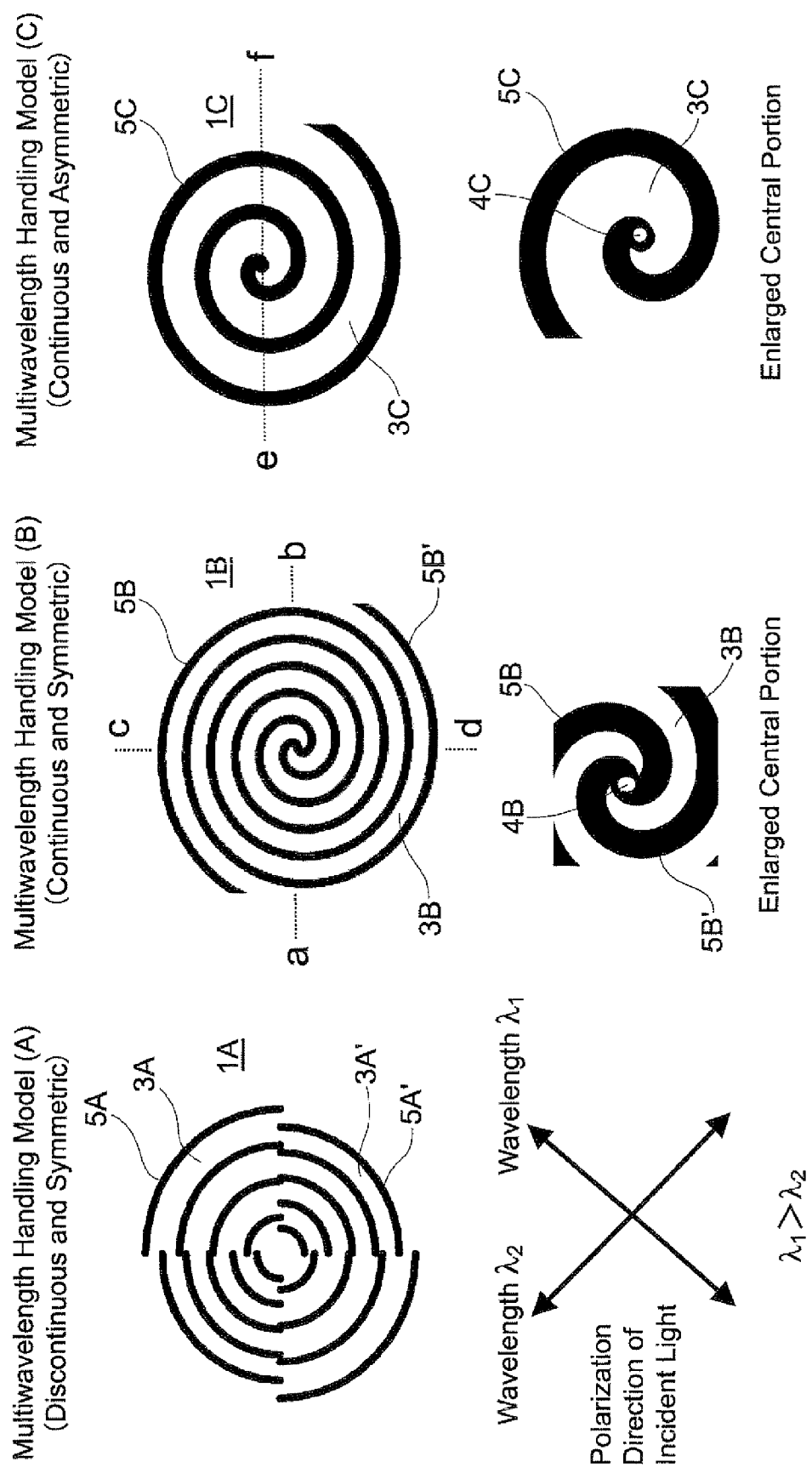
FIG. 7 shows top views and enlarged views of central portions of optical sensors according to a second example.

A pattern A (a model (A)) shown in FIG. 7 is one example of a sensor structure for solving the above problem. The pattern (A) includes a plurality of fan-shaped regions different in intervals of depressions 3A. More specifically, among four fan-shaped regions formed by dividing by 90 degrees a central angle of a circle on a substrate 1A, a plurality of the depressions 3A are concentrically arranged at intervals in two regions opposed to each other in relation to the center of the circle, while in the remaining two regions, a plurality of the depressions 3A' are concentrically arranged at intervals. In sum, the fan-shaped regions formed with the depressions 3A and the fan-shaped regions formed with the depressions 3A' are alternately arranged. Further, the intervals (pitches) between adjacent depressions 3A are wider than the intervals between adjacent depressions 3A'. Then, protrusions 5A and protrusions 5A' are formed between two adjacent depressions 3A and between two adjacent depressions 3A', respectively. In addition, on the substrate 1A formed with the depressions 3A, 3A' and the protrusions 5A, 5A', a metallic film (not shown) is formed as with the example 1.

As described above, in the pattern (A), the pitches in the pattern are changed depending on a direction (an angle around) from the center of the sensor. In this case, a direction corresponding to a pitch in the pattern is selected according to a specific wavelength (a wavelength λ1 or λ2) of excitation light and then the excitation light is allowed to polarize in the direction to generate a plasmon resonance. As a result, a plasmon wave can be efficiently converged to the center of the sensor. In the present example, a circle is divided into four fan-shaped regions to arrange alternately two regions whose pitches of the depressions are different from each other. Depending on the directivity performance of a polarization filter, however, the number of a fan-shaped region and a central angle can be varied.

A structure of the sensor resonating in a specific polarization direction is effective to a thin film with orientation and crystal anisotropy. Liquid crystal molecules, e.g., change in orientation direction according to an applied electric field thereto and then a polarization angle is rotated to detect the polarization angle where the Raman intensity is maximized, thereby enabling an orientation direction of molecules to be learnt. At the same time, by analyzing the Raman spectrum, the bonded state and molecular configuration of oriented molecules can be learnt.

(2) Pattern (B)

Figure 8:
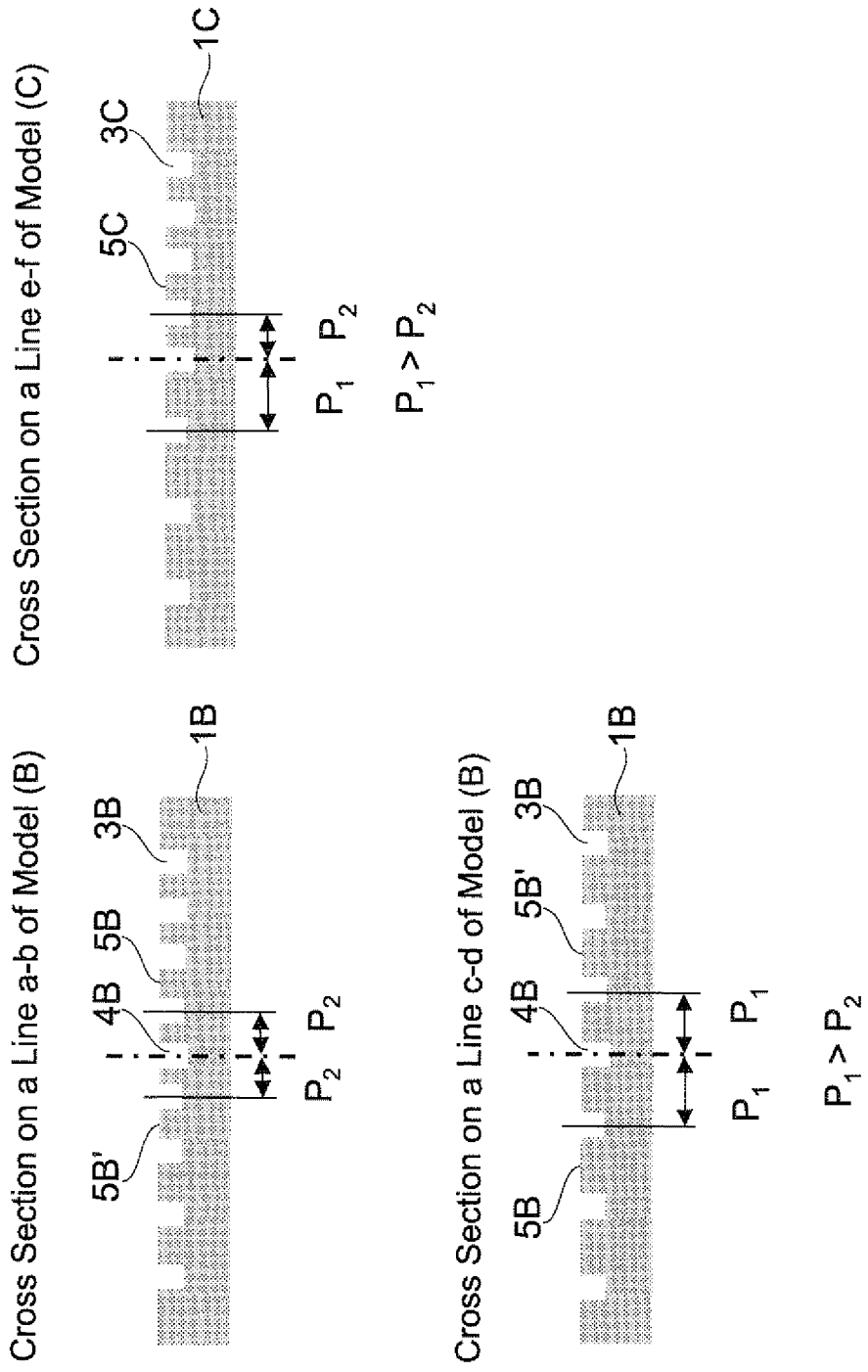
FIG. 8 shows respective cross-sectional views of the optical sensors shown in FIG. 7, in accordance with the second example.

A pattern (B) (a model B) shown in FIGS. 7, 8 is an example of a double-helical pattern provided in the optical sensor. This pattern (B) is formed of two helical protrusions 5B, 5B', which are joined with each other at the helical center. At the helical center, namely, at the center of the joint of the two protrusions 5B, 5B', is formed a substantially circular depression 4B with a smaller diameter than each of widths of the protrusions 5B, 5B'. Here, the substantially circular shape includes a circular shape, an elliptical shape with a different diameter depending on its angular direction and in addition to these shapes, further includes shapes approximate to other circles and other eclipses. Besides, the two helical protrusions 5B, 5B' are formed substantially in parallel to each other and between the protrusions 5B, 5B', a helical depression 3B is formed. Then, in cross sections on a line a-b and a line c-d which are perpendicular to each other, comparing intervals (pitches) between adjacent depressions 3B with each other, a pitch P1 in the cross section on the line c-d is smaller than a pitch P2 in the cross section on the line a-b. In addition, as with the example 1, on the substrate 1B, a metallic film (not shown) is formed.

As described above, in the cross section at the same central angle, the pattern (B) is bilaterally symmetric in relation to the helical center and the pitch of the depression is constant.

At the different central angles, however, the pitch continuously varies and therefore a plasmon resonance can be generated by excitation lights with continuous wavelengths. A filter capable of allowing a specific wavelength to pass through is set in an excitation light source with the continuous wavelengths to observe the intensity of Raman scattering light and changes in spectrum and thus a wavelength at which a resonant Raman effect occurs can be learnt. Further, as with the case of the pattern (A), by polarizing excitation light in a specific direction, an oriented state and anisotropy of a bonded state in molecules can be learnt.

(3) Pattern (C)

A pattern (C) shown in FIGS. 7, 8 is an example of one helical pattern provided in the optical sensor. The pattern (C) is formed of one helical protrusion 5C. At the helical center of the protrusion 5C, namely, the end of the helical center of the protrusion 5C, formed is a substantially circular depression 4C with a smaller diameter than a width of the protrusion 5C. Here, the substantially circular shape includes a circular shape, an elliptical shape formed with a different diameter depending on its angular direction and in addition to these shapes, further includes shapes approximate to other circles and other eclipses. Besides, a helical depression 3C is formed between the helical protrusions 5C. Then, in an interval (a pitch) between adjacent helical depressions 3C in a cross section on a line e-f, a leftward pitch P1 in relation to the helical center is larger than a rightward pitch P2 in relation to the same. In addition, as with the example 1, on the substrate 1C, a metallic film (not shown) is formed.

As described above, in the cross section at the same central angle, the pitch of the pattern (C) is bilaterally asymmetric in relation to the helical center. A plasmon resonance corresponding to a specific wavelength is generated on one side. There is, however, no problem with the convergence to the helical center, allowing the resolution of a resonant frequency to be enhanced. Besides, as with the pattern (B), a filter for allowing a specific wavelength to pass through is set in an excitation light source and thus a wavelength at which a resonant Raman effect occurs can be learnt. Further, as with the pattern (A), by polarizing light in a specific direction, an oriented state and anisotropy of a bonded state in molecules can be learnt.

Hereunder is a description of a process for fabricating the optical sensor according to the present invention.

Example 3

As a process for fabricating the sensor, other than a process for providing a concentric pattern on a metallic film made of silver or the like using a lift-off process, there is a process in which a concentric pattern is formed on a substrate using etching process and, a nanoimprint process and then a metallic film made of silver or the like is formed on the concentric pattern. There is no restriction on a material of a substrate, and silicon, glass, plastic, paper or the like may be employed.

(1) Substrate Etching Process

Figure 9:
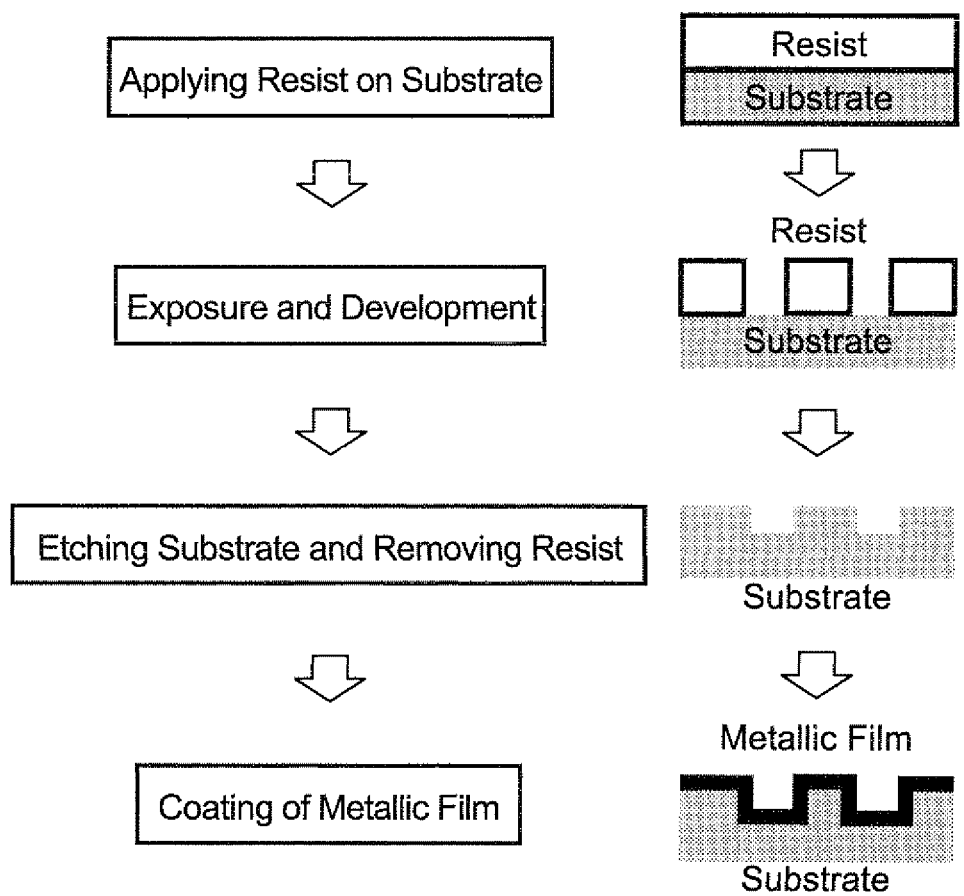
FIG. 9 is a flow chart of a substrate etching process, illustrating a process for fabricating an optical sensor according to a third example.

In a substrate etching process, as shown in FIG. 9, a resist is applied on a substrate and by removing partially the resist using optical exposure or electron beam exposure, and a fluxing material or the like (development), a resist pattern is formed. Then by a wet etching process and a dry etching process such as an ion etching process or a reactive ion etching process, the substrate is etched to form a pattern. Further, a metallic film made of a metal such as Ag, Au, Cu, Al or the like capable of exciting a plasmon is coated by a vapor-deposition process or a sputtering process to fabricate the sensor.

(2) Nanoimprint Process

Figure 10:
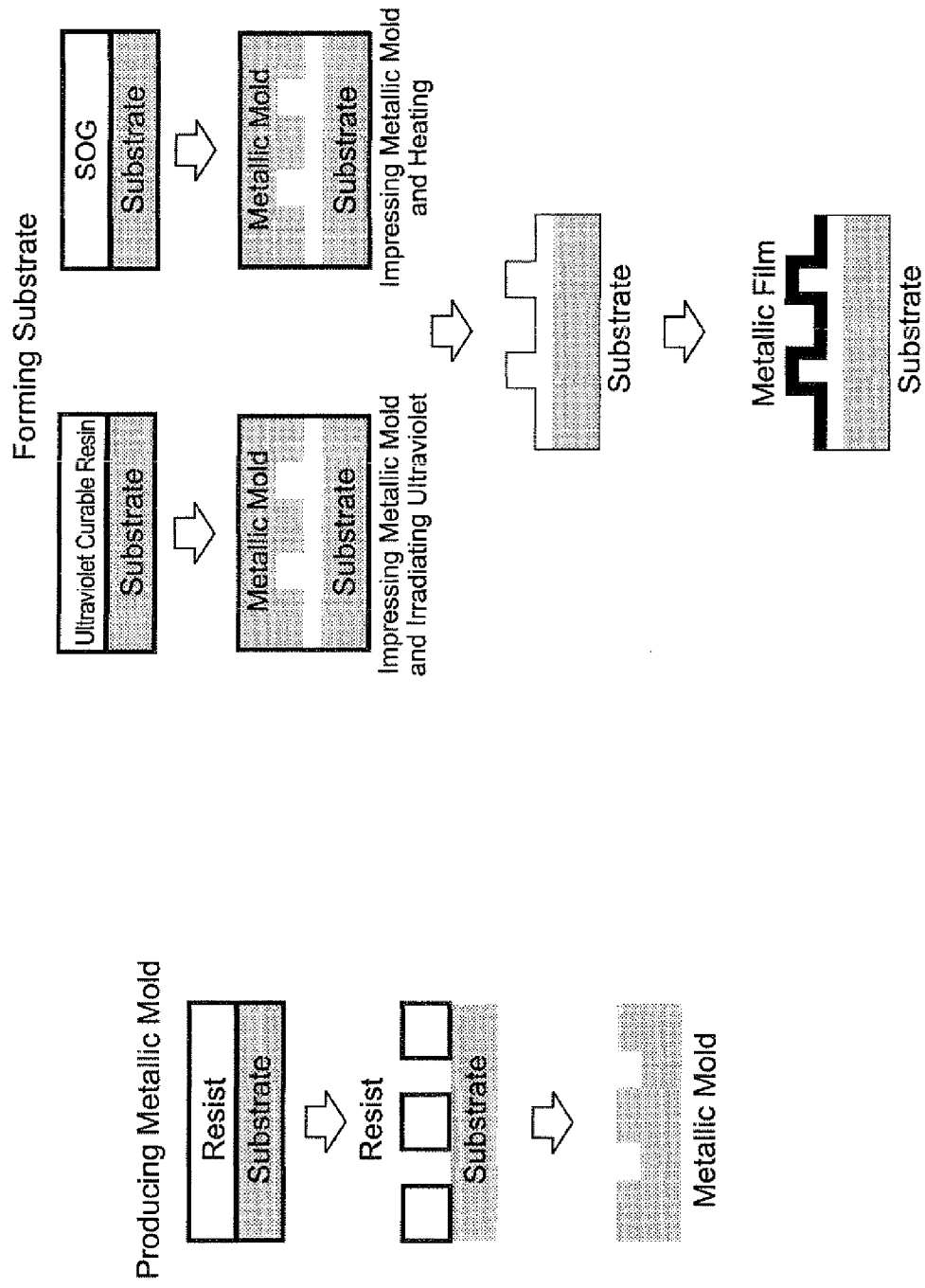
FIG. 10 is a flow chart of a nanoimprint process, illustrating a process for fabricating the optical sensor according to the third example.

In a nanoimprint process, as shown in FIG. 10, first, a metallic mold is produced and then by impressing the metallic mold to a substrate, a pattern-attached substrate is fabricated.

A resist is applied to the metallic mold and then the resist is removed partially using an optical exposure or an electron beam exposure, and a fluxing material. Then, the substrate is etched by a wet etching process, a dry etching process such as an ion etching process or a reactive ion etching process to form a pattern, thereby manufacturing the metallic mold. Besides, the surface of the substrate is coated with a low-surface-energy mold release agent such as fluorine resin or the like.

Then, with regard to the substrate, the substrate material is coated with an ultraviolet curable resin film, a sol-gel $SiO_2$ resin (SOG) film or the like and by impressing the metallic mold to the upper side of the substrate, a pattern is transferred to the ultraviolet curable resin film or the SOG film. In the case of the ultraviolet curable resin, after having cured the resin by irradiating an ultraviolet ray, the metallic mold is removed to fabricate a patterned substrate. Besides, in the case of the SOG film, after having cured the SOG film by heating at about 150 to about 200 degrees C., the metallic mold is removed to fabricate a patterned substrate. Further, by coating the upper side of the substrate with a film of a metal such as Ag, Au, Cu, Al or the like capable of exciting a plasmon, the sensor is fabricated using a vapor-depositing process or a sputtering process.

Example 4

Figure 11:
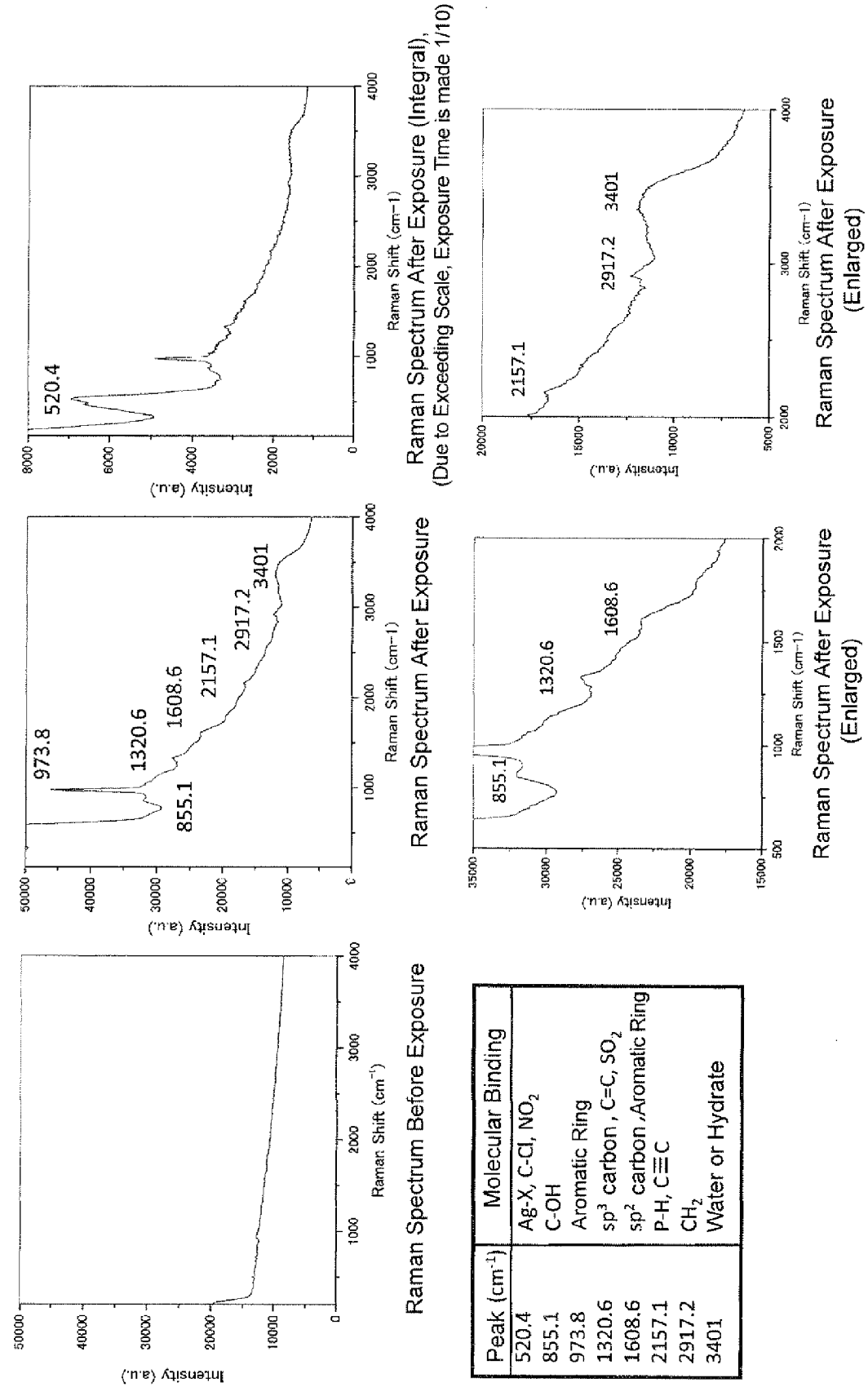
FIG. 11 shows Raman spectra of a fourth example.

After having left the optical sensor inside a chamber where no organic chemical is treated for two weeks with its sensor surface faced to an underneath of a wafer case (for the sake of preventing dusts from attaching thereto), the optical sensor was exposed to the atmosphere. As shown in FIG. 11, Raman spectra attributable to various organic and inorganic adsorbed substances and reactants were obtained. The detected substances are considered to be nitrate ions, sulfate ions, chlorides, hydrates and adsorbed organic substances (aromatic series).

Example 5

On the optical sensor fabricated in the example 1, a diamond-like carbon (DLC) film used for a magnetic disc was formed and its Raman spectrum was measured.

Figure 12:
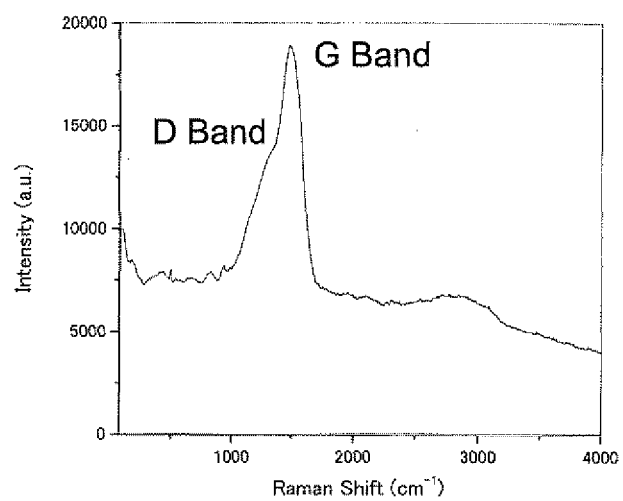
FIG. 12 shows a Raman spectrum of a fifth example.
Figure 13:
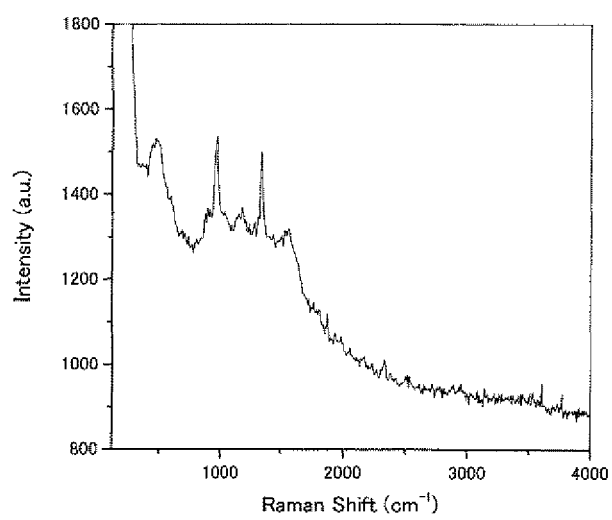
FIG. 13 shows a Raman spectrum of the fifth example.

When a DCL film 13 nm thick was formed, as shown in FIG. 12, peaks of a G band in 1,480 $cm^{-1}$ and D band near 1,300 $cm^{-1}$ were clearly observed. When a DCL film 0.8 nm thick was formed, as shown in FIG. 13, a number of peaks in 468 $cm^{-1}$, 974 $cm^{-1}$, 1,178 $cm^{-1}$, 1,339 $cm^{-1}$ and 1,554 $cm^{-1}$ and many peaks of organic substances in an initial stage of film growth were observed.

Further, on the optical sensor fabricated in the example 1, is formed a film of a lubricant agent made up of perfluoropolyesther (PEPE) which has a molecular configuration shown in a chemical formula 1 and is used for a magnetic disc. Then, its Raman spectrum was measured.

[Chemical formula 1]

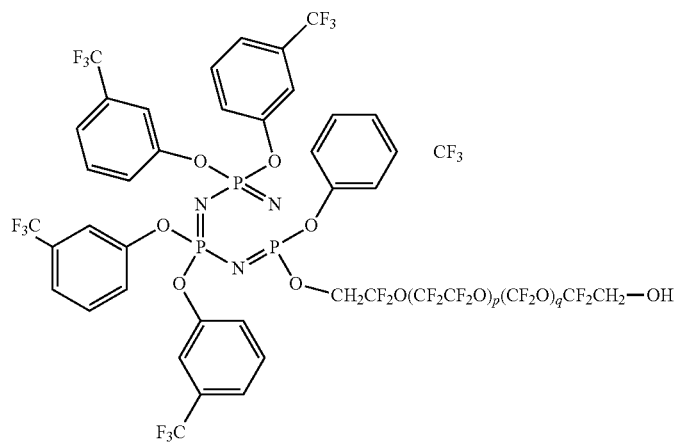

Figure 14:
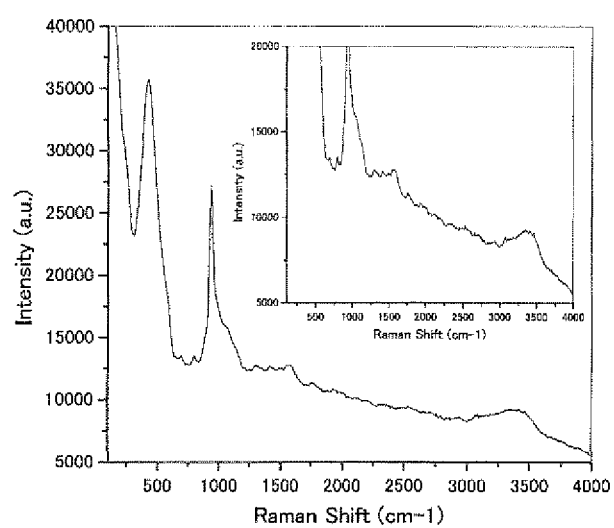
FIG. 14 shows a Raman spectrum of the fifth example.

When a PEPE film 2 nm thick was formed, as shown in FIG. 14, a number of peaks corresponding to the molecular configuration of PEPE were observed.

Using the optical sensor fabricated in the example 1, the configuration of a subnanometer thin film used for a magnetic disc could be analyzed.

DESCRIPTION OF THE SYMBOLS 1, 1A, 1b, 1C substrate
2 metallic film
3, 3A, 3B, 3C, 4, 4B, 4C depression
5B, 5B', 5C protrusion
6 self-assembled monolayer

The invention claimed is:

1. An optical sensor comprising:
a substrate;
a metallic film formed on the substrate, said metallic film including no apertures;
a circular depression formed in the center on a surface of said metallic film; and
a plurality of depressions concentrically formed on a surface of said metallic film at intervals with said circular depression defined as a center,
wherein, a diameter of said depression formed in the center is formed smaller than each of said intervals of a plurality of said depressions concentrically formed, whereby when light is irradiated to said metallic film, surface plasmon generated by surface plasmon resonance on a surface of said metallic film is allowed to concentrate on said depression formed in the center on said metallic film to enable surface-enhanced Raman scattering light to be observed from said depression formed in the center.

2. The optical sensor according to claim 1, comprising a plurality of fan-shaped regions defined by said depressions having varying intervals.

3. The optical sensor according to claim 1, comprising:
the substrate;
the metallic film formed on said substrate, said metallic film including no apertures:
the circular depression formed on the surface of said metallic film in the center thereof; and
the plurality of depressions concentrically formed on the surface of said metallic film at intervals of 450 to 530 nm with said circular depression defined as the center,
whereby when light is irradiated to said metallic film, surface plasmon generated by surface plasmon resonance on a surface of said metallic film is allowed to concentrate on said depression formed in the center on said metallic film to enable surface-enhanced Raman scattering light to be observed from said depression formed in the center.

4. The optical sensor according to claim 3, comprising a self-assembled monolayer on the surface of said metallic film.

5. The optical sensor according to claim 3, Wherein said metallic film is made of silver or gold.

6. The optical sensor according to claim 3, wherein said metallic film is made of silver to which bismuth is added.

7. An optical sensor comprising;
a substrate;
a metallic film formed on said substrate, said metallic film having no apertures;
two helical protrusions formed on a surface of said metallic film, said two protrusions being joined together at helical centers thereof, respectively; and
a substantially circular depression formed at said helical center, said substantially circular depression having a diameter less than a width of each of said protrusions,
whereby when light is irradiated to said metallic film, surface plasmon generated by surface plasmon resonance on a surface of said metallic film is allowed to concentrate on said depression formed in said helical center on said metallic film to enable surface-enhanced Raman scattering light to be observed from said depression in said helical center.

8. The optical sensor according to claim 7, comprising a self-assembled monolayer on the surface of said metallic film.

9. The optical sensor according to claim 7, where said metallic film is made of silver or gold.

10. The optical sensor according to claim 7, wherein said metallic film is made of silver to which bismuth is added.

11. An optical sensor comprising:
a substrate;
a metallic film formed on said substrate, said metallic film having no aperture;
one helical protrusion formed on a surface of said metallic film, and
a substantially circular depression formed at a helical center of said helical protrusion, said substantially circular depression having a diameter less than a width of said protrusion,
whereby when light is irradiated to said metallic film, surface plasmon generated by surface plasmon resonance on a surface of said metallic film is allowed to concentrate on said depression formed at said helical center on said metallic film to enable surface-enhanced Raman scattering light to be observed from said depression formed in said helical center.

12. The optical sensor according to claim 11, comprising a self-assembled monolayer on the surface of said metallic film.

13. The optical sensor according to claim 11, wherein said metallic film is made of silver or gold.

14. The optical sensor according to claim 11, wherein said metallic film is made of silver to which bismuth is added.

15. The optical sensor according to claim 3, wherein the circular depression has a diameter of 0.1 to 250 nm.

* * * * *